US009895458B2

(12) United States Patent
Hecht et al.

(10) Patent No.: US 9,895,458 B2
(45) Date of Patent: *Feb. 20, 2018

(54) ULTRAVIOLET DISINFECTING DEVICE FOR FOOD AND BEVERAGE DISPENSERS

(71) Applicant: AUTOMATIC BAR CONTROLS, INC., Vacaville, CA (US)

(72) Inventors: Thomas R. Hecht, Winters, CA (US); Richard A. Martindale, Vacaville, CA (US)

(73) Assignee: Automatic Bar Controls, Inc., Vacaville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/873,164

(22) Filed: Oct. 1, 2015

(65) Prior Publication Data
US 2016/0022849 A1 Jan. 28, 2016

Related U.S. Application Data

(63) Continuation-in-part of application No. 13/112,969, filed on May 20, 2011, now Pat. No. 9,192,191.
(Continued)

(51) Int. Cl.
A61L 2/10 (2006.01)
A23L 3/28 (2006.01)
(Continued)

(52) U.S. Cl.
CPC .............. A61L 2/10 (2013.01); A23L 3/28 (2013.01); A61L 2/00 (2013.01); A61L 9/00 (2013.01);
(Continued)

(58) Field of Classification Search
CPC ..... A61L 2/00; A61L 2/10; A61L 9/00; A23L 3/28; B67D 1/0086
See application file for complete search history.

(56) References Cited

U.S. PATENT DOCUMENTS 5,342,582 A * 8/1994 Horn ................. A61L 11/00
241/100
5,881,913 A 3/1999 Boulter
(Continued)

FOREIGN PATENT DOCUMENTS

WO 2009/098394 A1 8/2009
WO 2012015190 A2 2/2012

OTHER PUBLICATIONS

International Search Report and Written Opinion dated Aug. 17, 2011 in Int'l Patent Application No. PCT/US11/37405, 9 pages.
(Continued)

Primary Examiner — Regina M Yoo
(74) Attorney, Agent, or Firm — Kilpatrick Townsend & Stockton LLP

(57) ABSTRACT

Disinfecting devices and related methods are provided that apply germicidal ultraviolet light to disinfect dispensing components of food and beverage dispensers. A disinfecting holster for a nozzle of a beverage dispensing handle includes a housing adapted to receive a nozzle of a beverage dispensing handle and an ultraviolet light source bent around the housing to surround at least a portion of the housing. The ultraviolet light source generates and emits germicidal ultraviolet light onto the nozzle. The housing substantially contains the ultraviolet light within the housing during the application of the ultraviolet light to the dispensing nozzle. The ultraviolet light can be periodically applied to maintain the nozzle in a disinfected state.

21 Claims, 12 Drawing Sheets

Related U.S. Application Data

(60) Provisional application No. 61/346,805, filed on May 20, 2010.

(51) Int. Cl.
   *B67D 1/00* (2006.01)
   *A61L 2/00* (2006.01)
   *A61L 9/00* (2006.01)
   *B67D 1/07* (2006.01)

(52) U.S. Cl.
   CPC ........ *B67D 1/0086* (2013.01); *A61L 2202/15* (2013.01); *A61L 2202/16* (2013.01); *B67D 2001/075* (2013.01)

(56) References Cited

U.S. PATENT DOCUMENTS

| | | | |
|---|---|---|---|
| 6,077,427 A | 6/2000 | Burrows | |
| 6,135,838 A * | 10/2000 | Wang | A61L 9/205 445/22 |
| 6,832,487 B1 | 12/2004 | Baker | |
| 7,074,277 B2 | 7/2006 | Tuyls et al. | |
| 7,762,431 B1 | 7/2010 | Tuyls et al. | |
| 8,033,430 B2 | 10/2011 | Salmela et al. | |
| 8,353,882 B1 * | 1/2013 | Pelkus | A61M 37/00 604/290 |
| 2001/0010318 A1 | 8/2001 | Saveliev et al. | |
| 2002/0063954 A1 | 5/2002 | Horton, III | |
| 2004/0052680 A1 | 3/2004 | Elwood et al. | |
| 2004/0155201 A1 | 8/2004 | Russell et al. | |
| 2004/0166018 A1 * | 8/2004 | Clark | A61L 9/205 422/4 |
| 2007/0051901 A1 * | 3/2007 | Hopaluk | C02F 1/325 250/436 |
| 2007/0137726 A1 | 6/2007 | Yan | |
| 2009/0012459 A1 * | 1/2009 | Sobue | A61L 2/10 604/29 |
| 2009/0189084 A1 | 7/2009 | Pinsky | |
| 2009/0277927 A1 | 11/2009 | Schroeder et al. | |
| 2010/0000618 A1 | 1/2010 | Bertucci et al. | |
| 2011/0286883 A1 | 11/2011 | Hecht et al. | |

OTHER PUBLICATIONS

Non-Final Office Action dated May 9, 2013 in U.S. Appl. No. 13/112,969, 10 pages.
Final Office Action dated Sep. 20, 2013 in U.S. Appl. No. 13/112,969, 10 pages.
Extended European Search Report dated Feb. 20, 2014 in European Patent Application No. 11784351.6, 7 pages.
Non-Final Office Action dated Apr. 24, 2014 in U.S. Appl. No. 13/112,969, 15 pages.
Final Office Action dated Aug. 20, 2014 in U.S. Appl. No. 13/112,969, 13 pages.
Non-Final Office Action dated Jan. 28, 2015 in U.S. Appl. No. 13/112,969, 15 pages.
Notice of Allowance dated Jul. 13, 2015 in U.S. Appl. No. 13/112,969, 8 pages.
International Search Report and Written Opinion dated Jan. 13, 2017 in International Patent No. PCT/US2016/054979, 12 pages.

\* cited by examiner

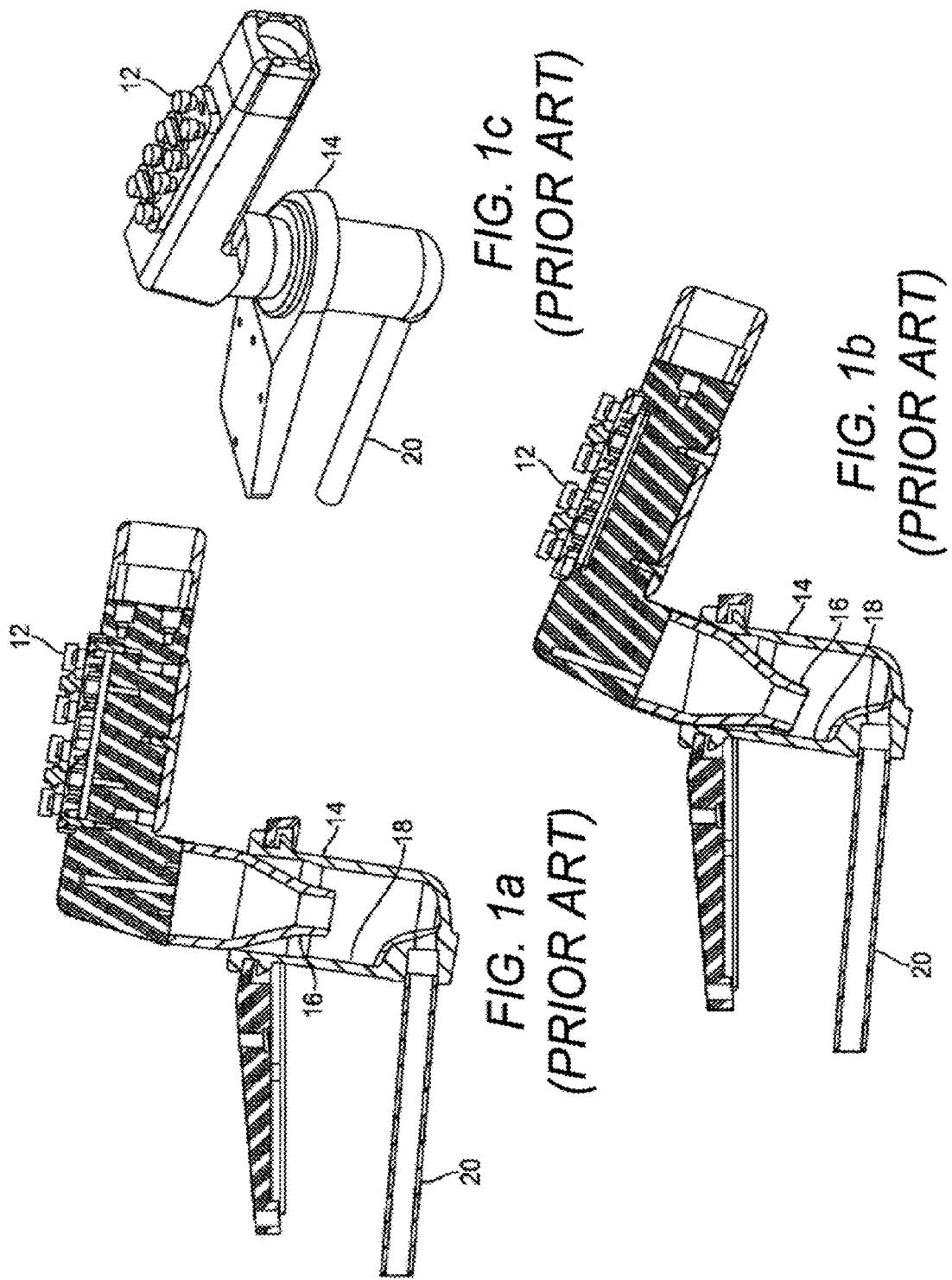

ULTRAVIOLET DISINFECTING DEVICE FOR FOOD AND BEVERAGE DISPENSERS

CROSS-REFERENCES TO RELATED APPLICATIONS

This application is a continuation in part of U.S. application Ser. No. 13/112,969 entitled "Ultraviolet Disinfecting Device for Food and Beverage Dispensers," filed May 20, 2011 which claims the benefit of U.S. Provisional Application No. 61/346,805, entitled "Ultraviolet Disinfecting Device for Food and Beverage Dispensers," filed May 20, 2010, the entire disclosures of which are hereby incorporated herein by reference.

BACKGROUND

The present invention is related to food and beverage dispensers, and more specifically to a method and means to provide ultraviolet disinfection of dispensing points of food and beverage dispensers.

Food and beverage dispensers can become contaminated with molds and/or bacteria. Such molds and/or bacteria can then be inadvertently passed along for consumption, thereby posing a potential health threat. Such contamination can occur in various ways.

For example, FIGS. 1a, 1b, and 1c show a known bar gun 12 (or beverage dispenser) that is placed in its holster 14. Such a bar gun 12 and holster 14 set up is commercially available from the assignee of this patent application. FIG. 1a depicts the general position of the dispensing nozzle 16 of the bar gun 12 as it is being inserted into the holster 14, while being supported by the operator's hand. FIG. 1b depicts the at-rest (or unsupported) position of the bar gun 12 when stowed in the holster 14. The weight of the tubing bundle (not shown) attached to the bar gun 12, along with location of the center of gravity of the bar gun 12 relative to the holster 14, can cause the dispensing nozzle 16 to come into direct contact with the potentially contaminated interior surface 18 of the holster 14. The holster-based solution includes a generally cylindrical member that is configured to accept and encompass the nozzle of the bar gun, and provide a collection device for fluid discharged by the bar gun. This collection device may or may not be fitted with a drainage means, such as the drain line 20 shown. Additionally, while the collection device does provide for collection of fluid discharged from the dispensing nozzle 16 of the bar gun 12, continued use may cause a build-up on the interior surface 18 of the holster 14 as the fluids dry. Furthermore, if not regularly attended to, the interior surface 18 of the collection device can provide a medium for the growth of bacteria and/or molds. The size of the collection device can also readily allow for contact between the dispensing nozzle 16 and the inner surface 18 of the collection device, and thus potentially contaminating the dispensing nozzle through which the next beverage is dispensed to a customer.

Additionally, existing beverage dispensers, for example, hand-held beverage dispensers (e.g., a bar gun), are prone to contamination due to frequent handling by one or more users (who may have less than sanitary hands). Additionally, the residue of fluids dispensed by beverage dispensers often provides an environment that supports the growth of molds and/or bacteria either airborne or deposited by unsanitary contact. Such molds and/or bacteria may then be transferred into a dispensed beverage that is then consumed.

There is therefore a need to provide a way to disinfect food and beverage dispensers to avoid dispensing food and/or beverages that contain pathogens such as molds and/or bacteria.

BRIEF SUMMARY

The present invention provides a method and means to disinfect dispensing components of food and beverage dispensers (e.g., a dispensing port of a food dispenser, a dispensing nozzle of a beverage dispenser). The dispensing components are subjected to contained ultraviolet radiation of adequate duration and intensity to disinfect the dispensing components. Various approaches can be used to trigger the application of the ultraviolet light, such as by triggering the application when a beverage dispenser such as a bar gun is returned to its support, and/or activation at regular intervals (e.g., intervals not exceeding a maximum period of non-activation). To enhance the impact of the applied ultraviolet light, some or all of the dispensing components can be made from materials that can be at least partially penetrated by ultraviolet light (e.g., ultraviolet transparent (UVT) materials) to pass the ultraviolet light onto surfaces potentially in need of disinfection, while being suitable for food contact (e.g., NSF/ANSI Std. 51 materials (National Sanitation Foundation—Food Equipment Materials). The ultraviolet light can also be used to generate ozone for additional germicidal and/or deodorant action. The generated ozone can be applied to the dispensing components to penetrate into areas that the ultraviolet light does not reach.

Thus, in one aspect, a disinfecting holster for a nozzle of a beverage dispensing handle is provided. The disinfecting holster includes a housing adapted to receive a nozzle of a beverage dispensing handle, an ultraviolet light source arranged around at least a portion of the housing, and a first enclosure defining a first chamber holding the housing and containing the ultraviolet light source. The ultraviolet light source configured to generate and emit germicidal ultraviolet light onto the housing and the nozzle. The first enclosure having a top surface including a nozzle opening aligned with the housing and configured to hold the nozzle of the beverage dispensing handle such that only the nozzle extends into the housing.

In some embodiments, the ultraviolet light source may be a U-bend ultraviolet light source. In other embodiments, the ultraviolet light source may be an O-ring ultraviolet light source. The ultraviolet light source may be formed of a plurality of ultraviolet light source modules that surround at least the portion of the housing.

An interior of the housing may be formed of or lined with food-grade ultraviolet-transmissive plastic. An exterior of the housing may be formed of or lined with transmissive quartz sleeve to protect the ultraviolet light source from spatters coming out of the nozzle.

The first enclosure may be formed on top of a second enclosure defining a second chamber. The first enclosure and the second enclosure may be separated by a perforated surface provided at a bottom of the first enclosure. The perforated surface may be formed of or lined with reflective material to reflect the ultraviolet light into an orifice of the nozzle. The first enclosure may include a fan to distribute ozone generated by the ultraviolet light within the first enclosure and the housing.

The disinfecting holster may further comprise a controller configured to periodically activate the ultraviolet light source to maintain the nozzle in a disinfected state. The controller provides for a manually-initiated application of ultraviolet light.

In another aspect, a method for disinfecting a nozzle of a beverage dispensing handle is provided. The method includes arranging an ultraviolet light source around at least a portion of a nozzle of a beverage dispensing handle, and emitting germicidal ultraviolet light by the ultraviolet light source onto the nozzle. The ultraviolet light source is provided within a housing that substantially contains the ultraviolet light and the ultraviolet light is emitted by the ultraviolet light source with a duration and an intensity selected to disinfect the nozzle.

In some embodiments, the ultraviolet light source may be a U-bend ultraviolet light source. In other embodiments, the ultraviolet light source may be an O-ring ultraviolet light source.

The step of emitting germicidal ultraviolet light may also include controlling an activation of an ultraviolet light source via a controller configured to periodically activate the ultraviolet light source to maintain the nozzle in a disinfected state. The step of emitting germicidal ultraviolet light onto the nozzle may also include manually initiating the emission of the ultraviolet light. The step of emitting germicidal ultraviolet light onto the nozzle may also include emitting the light from a plurality of ultraviolet light source modules distributed around the housing.

An interior of the housing may be formed of or lined with food-grade ultraviolet-transmissive plastic. An exterior of the housing may be formed of or lined with transmissive quartz sleeve to protect the ultraviolet light source from spatters coming out of the nozzle.

In another aspect, an apparatus for disinfecting a nozzle of a beverage dispensing handle is provided. The apparatus comprises a housing adapted to receive a nozzle of a beverage dispensing handle, an ultraviolet light source arranged around at least a portion of the housing, a first enclosure defining a first chamber containing the ultraviolet light, and a second enclosure defining a second chamber provided below the first enclosure. The ultraviolet light source is configured to generate and emit germicidal ultraviolet light onto the nozzle. The first enclosure has a top surface including a nozzle opening aligned with the housing and configured to hold the nozzle of the beverage dispensing handle such that only the nozzle extends into the housing. The second enclosure is separated from the first enclosure by a perforated surface. An interior of the housing is formed of or lined with food-grade ultraviolet-transmissive plastic, and an exterior of the housing is formed of or lined with transmissive quartz sleeve to protect the ultraviolet light source from spatters coming out of the nozzle.

For a further understanding of the nature and advantages of the invention, reference should be made to the following description taken in conjunction with the accompanying figures. It is to be expressly understood, however, that each of the figures is provided for the purpose of illustration and description only and is not intended as a definition of the limits of the embodiments of the present invention.

BRIEF DESCRIPTION OF THE DRAWINGS

FIG. 1a shows a known bar gun positioned relative to a cylindrical holster as held by a user during its insertion into the holster.

FIG. 1b shows a typical position of known bar gun relative to a cylindrical holster after it has been released by the user.

FIG. 1c shows a perspective view of the known bar gun and cylindrical holster of FIG. 1a.

DETAILED DESCRIPTION

Figure 2A:
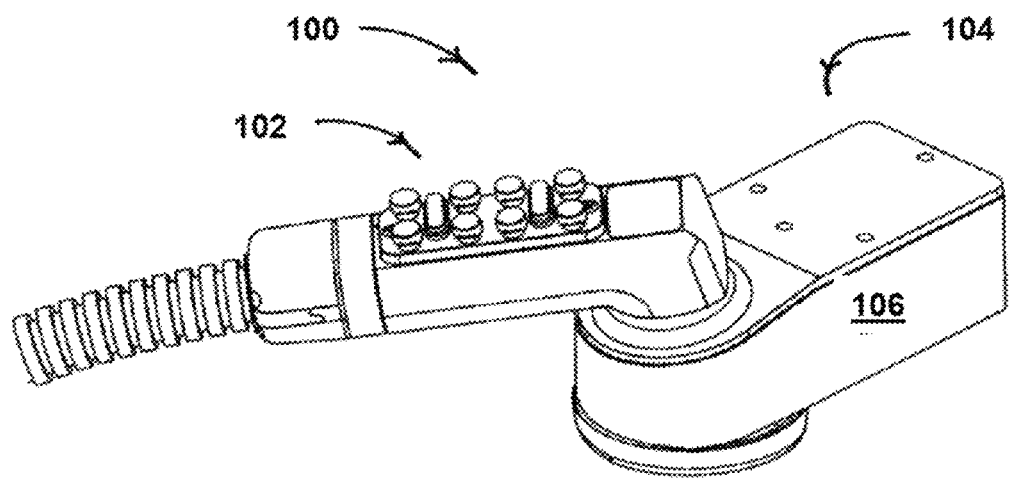
FIGS. 2a through 2e illustrate a bar gun holster configured to apply contained ultraviolet light to disinfect dispensing components of the bar gun, in accordance with an embodiment of the present invention.

The invention described herein provides methods and means to disinfect dispensing components of food and beverage dispensers. Contained ultraviolet light is applied to the dispensing components to kill molds and/or bacteria on the components. The ultraviolet light can be applied with a sufficient intensity and duration to provide a desired level of disinfection. The ultraviolet light can also be used to generate ozone, which can be used to provide additional disinfection and/or deodorant action, and can be distributed to reach areas of dispensing components not reached by the applied ultraviolet light.

Ultraviolet Disinfection Devices

FIGS. 2a through 2e illustrate a bar gun assembly 100 that includes a bar gun 102 and a holster 104 configured to apply contained ultraviolet light to disinfect dispensing components of the bar gun 102. The holster 104 includes an outer wall 106 that helps to prevent emission of ultraviolet light from the holster 104 during an application of ultraviolet light by the holster 104 onto dispensing components of the bar gun 102 (e.g., nozzle 108).

Figure 2B:
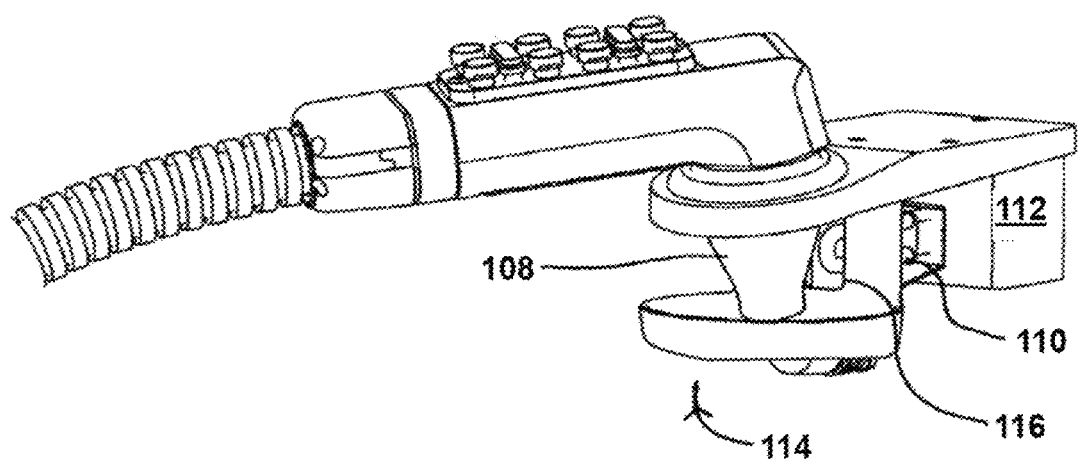
Figure 2C:
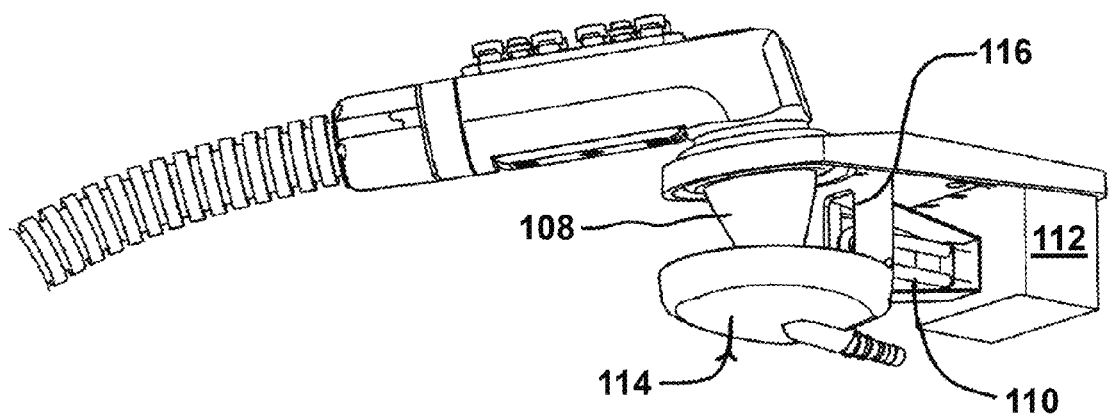
Figure 2D:
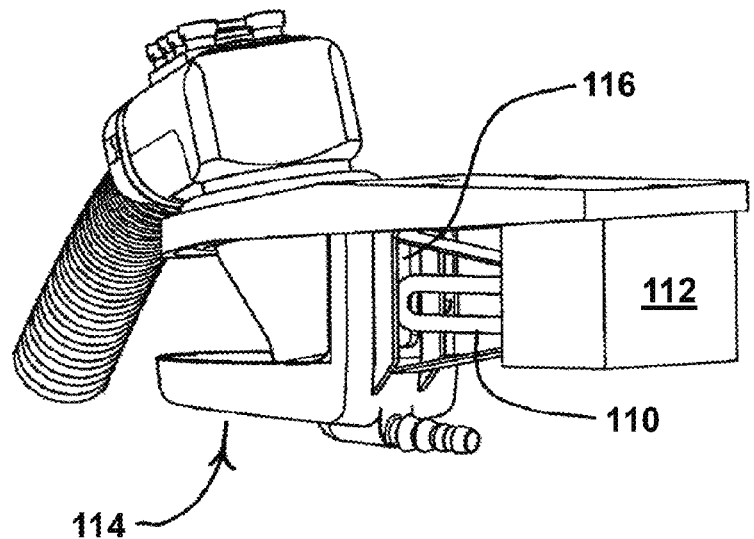

FIG. 2a shows the bar gun 102 stowed in the holster 104. FIGS. 2b through 2d illustrate internal components of the holster 104 (outer wall 106 not shown to avoid obscuring the internal components). The holster 104 includes an ultraviolet light source (e.g., a germicidal lamp or tube lamp 110) mounted in the holster 104 via a lamp mount 112. A germicidal ballast (not shown) for the tube lamp 110 can be mounted within the lamp mount 112. The holster 104 further includes a nozzle receiving portion 114 that accommodates the nozzle 108 when the bar gun 102 is stowed, thereby positioning the nozzle 108 to receive germicidal ultraviolet light emitted by the tube lamp 110. Ultraviolet light emitted by the tube lamp 110 enters the nozzle receiving portion 114 by way of an aperture 116 positioned between the tube lamp and the nozzle receiving portion. One or more inner surfaces of the nozzle receiving portion can be configured (e.g., via a surface finish, an applied surface layer, and via its shape) to reflect ultraviolet light so that ultraviolet light entering through the aperture 116 is reflected onto the nozzle 108 from all sides, including from the bottom so that the ultraviolet light enters into the orifice of the nozzle to at least some extent. For example, the outer wall 106 can be shaped and include an internal reflective surface that evenly distributes the ultraviolet light entering through the aperture 116 to all sides of the nozzle 108.

The holster 104 and/or the bar gun 102 can be configured with a means that senses when the bar gun is stowed in the holster. For example, known switches, contacts, proximity sensors, etc., can be used to sense when the bar gun is stowed. Control circuitry (not shown) can used to activate the tube lamp 110 at suitable times and intervals. The control circuitry can be mounted in a suitable location (e.g., within the lamp mount 112). Although a variable intensity can be used, in many embodiments the ultraviolet light source is configured to emit ultraviolet light at an intensity known to provide a suitable level of disinfection. The control circuitry can keep track of suitable parameters (e.g., time since last ultraviolet application, usage parameters of the bar gun, etc.) to provide periodic applications of ultraviolet light suitable to maintain the nozzle of the bar gun in a disinfected state. In many embodiments, the control circuitry limits the application of ultraviolet light to when the bar gun is stowed and stops any application of ultraviolet light upon removal of the bar gun from the holster. A means to manually initiate the application of ultraviolet light can also be provided (e.g., via a switch, button, control panel interface, etc.).

The holster 104 can also be configured to distribute ozone generated by the ultraviolet light to provide further disinfection and/or deodorant action to dispensing components of the bar gun 102. For example, the holster 104 can further include a circulation means (e.g., a fan) to circulate ozone around the interior of the holster 104 to enhance distribution of ozone around the nozzle 108.

Figure 2E:
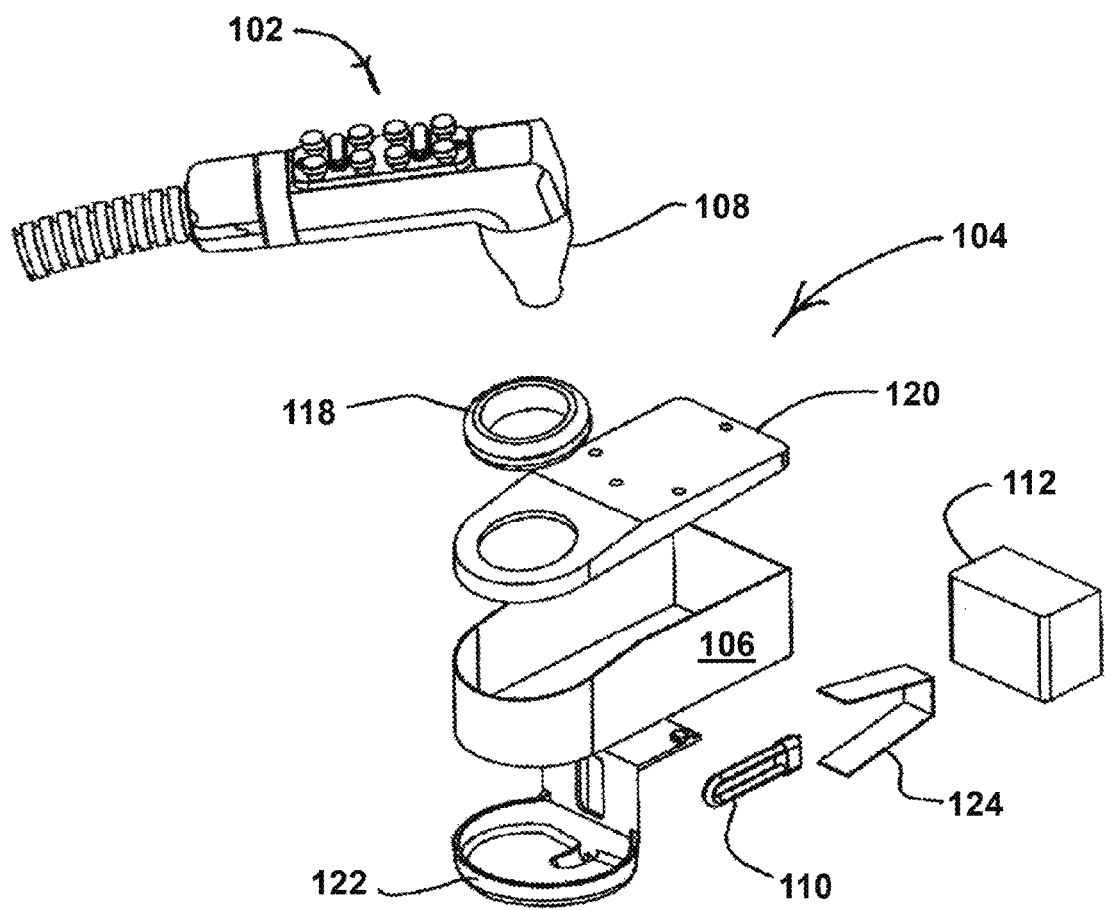

FIG. 2e is an exploded view of the holster 104. The holster 104 includes a grommet 118, a top cover 120, the outer wall 106, a drip collection member 122, the tube lamp 110, a reflector 124, and the lamp mount 112. Components of the holster 104 not shown include the control circuitry for activating the lamp 110, and the above-discussed means for sensing when the bar gun 102 is stowed in the holster. The grommet 118 and the nozzle 108 can be configured with mutually shaped portions to establish and maintain a substantial seal between the nozzle 108 and the grommet 118 when the bar gun is stowed in the holster, thereby preventing the escape of ultraviolet light from the holster and enhancing the concentration of any ozone generated within the holster.

Figures 3A, 3B:
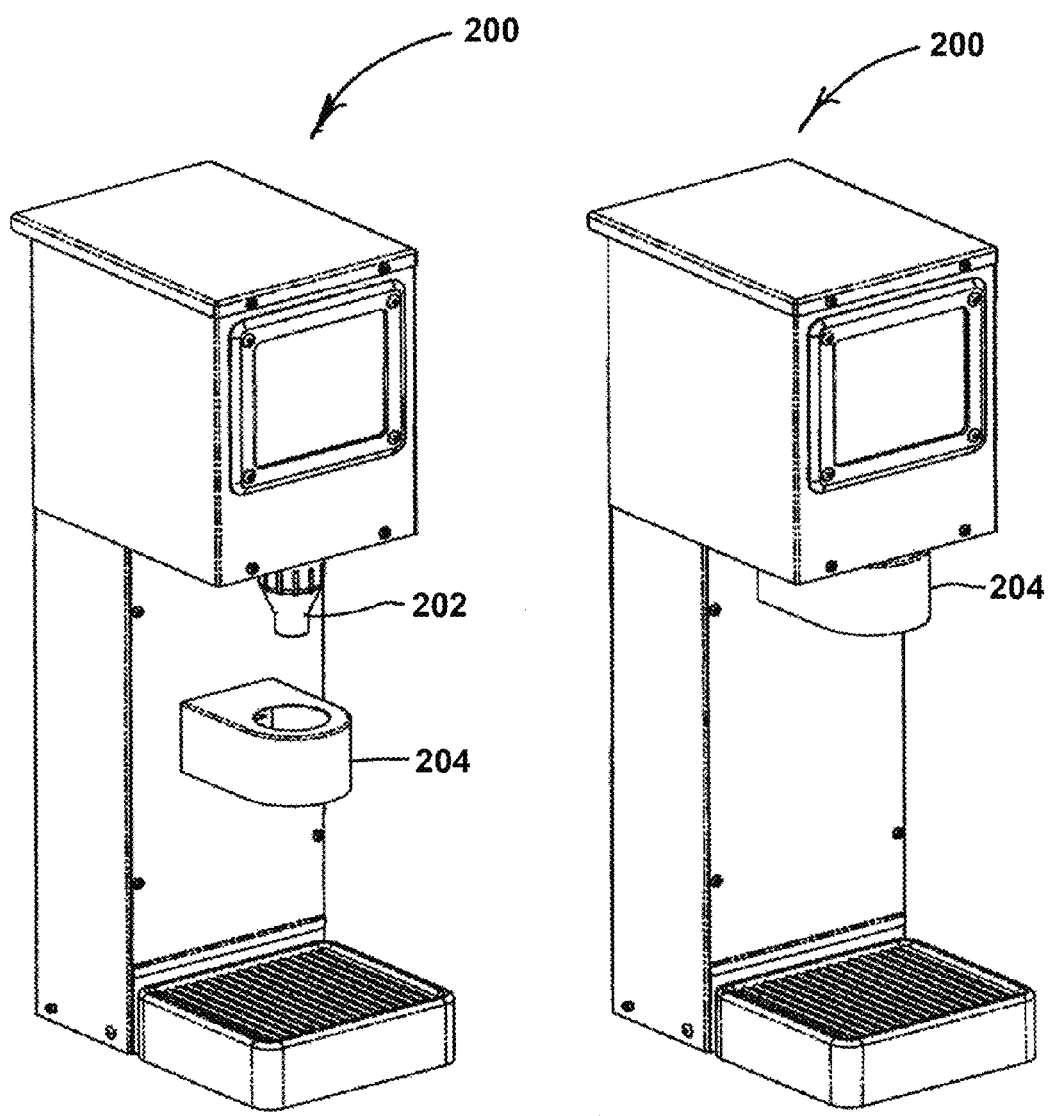
FIGS. 3a and 3b illustrate a beverage dispensing tower configured to apply contained ultraviolet light to disinfect dispensing components of the dispensing tower, in accordance with an embodiment of the present invention.

The above-discussed ultraviolet disinfection can be applied to other types of beverage dispensers. For example, FIGS. 3a and 3b illustrate a beverage dispensing tower 200 configured to periodically apply contained ultraviolet light to disinfect dispensing components (e.g., nozzle 202) of the dispensing tower 200. The beverage dispensing tower 200 includes a disinfecting chamber 204 that is movable to surround the nozzle 202 so that ultraviolet light can be applied to the nozzle 202 in a contained manner. FIG. 3a shows the disinfecting chamber 204 disengaged from the nozzle 202. And FIG. 3b shows the disinfecting chamber 204 positioned to surround the nozzle 202 to contain ultraviolet light during an application of ultraviolet light to the nozzle 202. The ultraviolet light applied can be generated, for example, via an ultraviolet light source mounted within the disinfecting chamber 204, or can be mounted in a suitable location exterior to the disinfecting chamber 204 and the ultraviolet light introduced into the disinfecting chamber (e.g., via an aperture as disclosed above, via one or more fiber optic cables, or via any other suitable known transmission means). Suitable control circuitry, such as discussed above, can be mounted in a suitable location and used to control an actuation of the disinfecting chamber to position the disinfecting chamber and the application of ultraviolet light to provide periodic applications of ultraviolet light, as discussed above with reference to the holster 104.

Figure 4A:
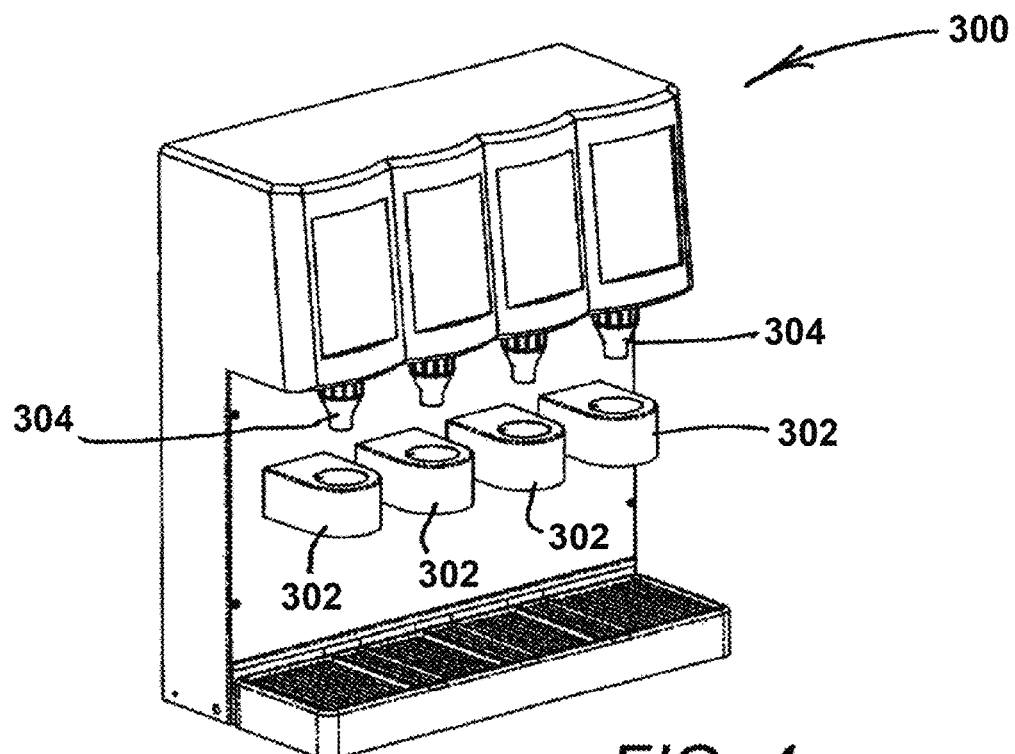
FIGS. 4a and 4b illustrate a multi-nozzle beverage dispensing tower configured to apply contained ultraviolet light to disinfect dispensing components of the multi-nozzle dispensing tower, in accordance with an embodiment of the present invention.
Figure 4B:
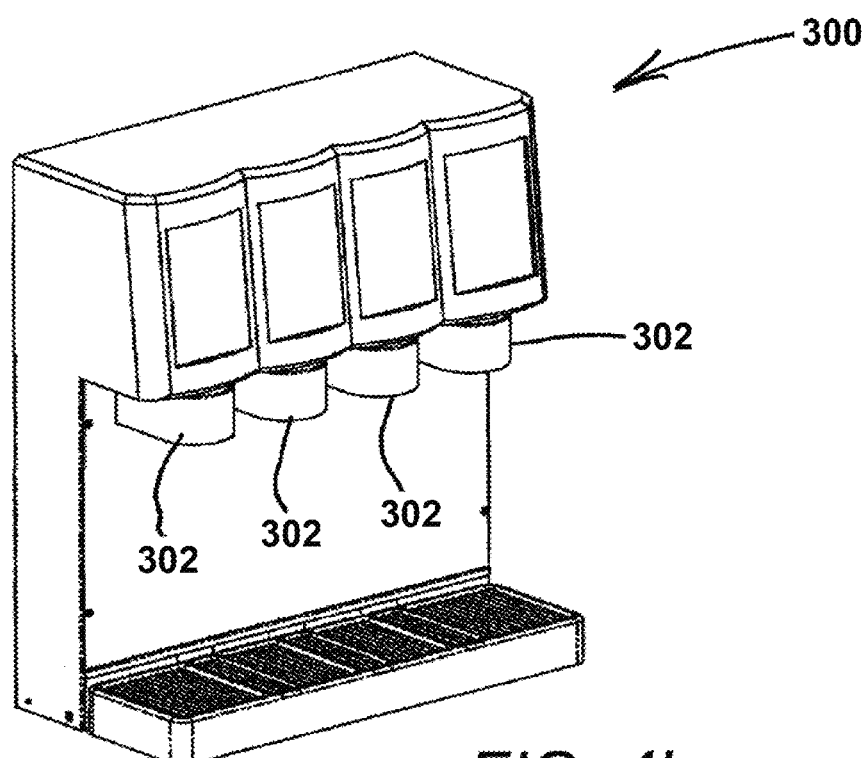

FIGS. 4a and 4b illustrate a similar application of ultraviolet disinfection to a multi-nozzle beverage dispensing tower 300. The multi-nozzle beverage dispensing tower 300 can include multiple disinfecting chambers 302 corresponding to multiple nozzles 304 as illustrated. Alternatively, any number of the disinfecting chambers can be integrated into one or more common disinfecting chambers configured to surround any suitable number of the nozzles during an application of ultraviolet light. The multi-nozzle beverage dispensing tower 300 can include, for example, any of the applicable features and/or functionality discussed above with respect to the holster 104 and the beverage dispensing tower 200.

Figure 5A:
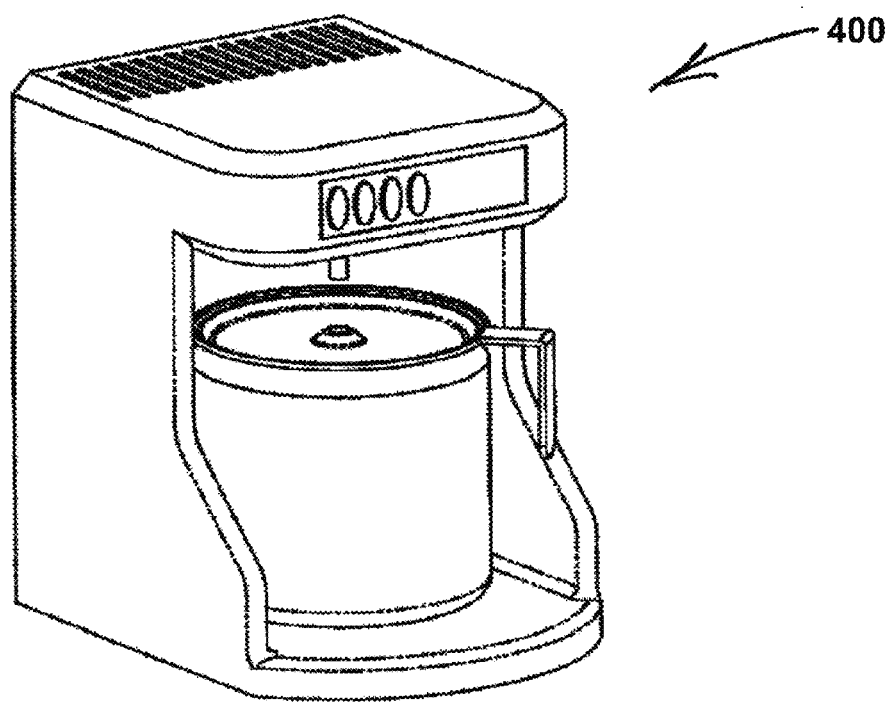
FIGS. 5a and 5b illustrate a coffee maker configured to apply contained ultraviolet light to disinfect dispensing components of the coffee maker, in accordance with an embodiment of the present invention.
Figure 5B:
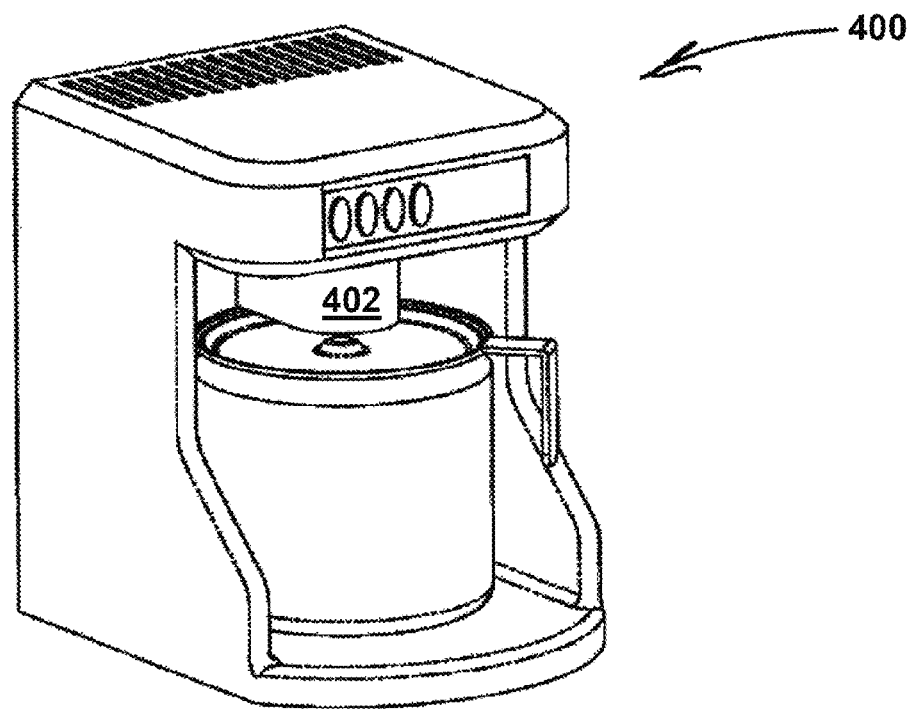

FIGS. 5a and 5b illustrate a coffee maker 400 configured to apply contained ultraviolet light to disinfect dispensing components of the coffee maker 400. The coffee maker 400 includes a disinfecting chamber 402 that can be positioned (e.g., attached, moved, actuated, etc.) for the application of ultraviolet light to dispensing components of the coffee maker 400. The coffee maker 400 can include, for example, any of the applicable features and/or functionality discussed above with respect to the holster 104, the beverage dispensing tower 200, and the multi-nozzle beverage dispensing tower 300.

FIGS. 8a through 8e illustrate another exemplary a bar gun holster configured to apply contained ultraviolet light to disinfect dispensing components of the bar gun, in accordance with an embodiment of the present invention. FIGS. 8a through 8e illustrate similar features to FIGS. 2a through 2e. The reference numerals for these elements are kept the same and a discussion of these elements is provided above. Accordingly, the discussion of these similar elements is omitted below with respect to FIGS. 8a through 8e.

The bar gun holster 800 illustrated in FIGS. 8a through 8e includes a support surface 821 configured to interface with a beverage dispensing handle (e.g. a bar gun 102) to support the bar gun 102 when stowed in the holster 800. The holster 800 may also include a receiving housing 814 coupled with the support surface 821 configured to receive the nozzle 108 of the bar gun 102 when the bar gun 102 is stowed in the holster 800. The holster 800 may also include an ultraviolet light source 802 that surrounds at least a portion of the receiving housing 814. For example, the ultraviolet light source 802 may include a U-bend (e.g. horseshoe shaped, U-shaped) lamp. The U-bend lamp may be provided around the receiving housing 814. When the bar gun 102 is coupled to the bar gun holster 800 (e.g. when the bar gun 102 is stowed in the bar gun holster 800), the U-bend lamp surrounds the nozzle 108 of the bar gun 102. One of ordinary skill in the art will appreciate that even though a U-shaped shaped lamp is illustrated in FIGS. 8a through 8e as the ultraviolet light source 802, the ultraviolet light source can be a ring-shaped (e.g. O-bend, O-shaped, O-ring) lamp that completely surrounds the receiving housing 814. According to various embodiments, the ultraviolet light source 802 may be continuous and/or one-piece (e.g. a U-bend lamp or an O-ring). Alternatively, the ultraviolet light source 802 may be formed of multiple ultraviolet light source modules (e.g. multiple ultraviolet light emitting lamps) provided around the receiving housing 814 to surround at least a portion of the nozzle 108 when provided within the receiving housing 814.

In some embodiments, the receiving housing 814 may be provided at an angle with respect to the ultraviolet light source 802 such that more ultraviolet rays may fall on the nozzle 104 when the nozzle is provided in the receiving housing 814. The bar gun holster 800 may include a raised surface 828 to accommodate the nozzle 108 of the bar gun 102 at an angle.

The extremities of the ultraviolet light source 802 may be coupled to corresponding tube sockets 804 via, for example, contact pins. The ultraviolet light source 802 may be coupled to the tube socket(s) 804 by any suitable means. The ultraviolet light source 802 illustrated in FIGS. 8a through 8e emits ultraviolet light on the nozzle from multiple angles around the nozzle 108 to sanitize/sterilize the nozzle 108. The embodiment illustrated in FIGS. 8a through 8e effectively sanitizes both the tip and upper body portion of the nozzle 108.

According to various embodiments, an interior surface of the receiving housing 814 may be molded to have a similar shape to the nozzle 108 so as to snugly hold the nozzle 108 in place. The receiving housing 814 may have an opening 816 through which the nozzle 108 may be inserted into the receiving housing 814. In some embodiments, an interior surface of the receiving housing 814 that faces the nozzle 108 (when the nozzle 108 is stowed in the receiving housing 814) may be formed of or lined with food-grade ultraviolet-transmissive plastic 818. An exterior of the receiving housing 814 may be formed of or lined with quartz sleeve 820 to act as a shield to protect the electronics and the ultraviolet light source 802 from spatters that may come out of the nozzle 108. The quartz sleeve 820 may be fully transmissive to allow the ultraviolet light emitted from the ultraviolet light source 802 to be transmitted onto the nozzle 108.

The bar gun holster 800 may include a drip pan 806 having a plurality of perforations 807 (e.g. holes) to allow for any liquid remaining in or dripping from the nozzle 108 to flow through. According to various embodiments, the perforated drip pan 806 may be coated with a reflective material to reflect the ultraviolet light so that ultraviolet light is reflected onto the nozzle 108 from the bottom so that the ultraviolet light enters into the orifice of the nozzle 108 to disinfect the interior surface of the nozzle 108 as well.

An enclosed disinfecting chamber 812 may be provided above the drip pan 806 to house the ultraviolet light source 802 and the nozzle 108. The enclosed disinfecting chamber 812 may be defined by a top wall 822, side wall 824, front wall 834 and the drip pan 806 at the bottom. The bar gun holster 800 can also be configured to distribute ozone generated by the ultraviolet light to provide additional disinfection and/or deodorant action to the nozzle 108 of the bar gun 102. For example, the disinfecting chamber 812 can further include a circulation means (e.g., a fan) to circulate ozone around the interior of the disinfecting chamber 812 and the receiving housing 814 to enhance distribution of ozone around the nozzle 108. The enclosed disinfecting chamber 812 and the receiving housing 814 may be in communication such that the ozone gas generated by the ultraviolet light source 802 provided in the disinfecting chamber 812 can travel into the receiving housing 814 to further disinfect the nozzle 108.

A drip collection chamber 810 may be provided below the drip pan 806 to collect the liquid dripping from the nozzle 108. The drip collection chamber 810 may be defined by the bottom of the disinfecting chamber 812 on the top, side wall 826, front wall 836 and bottom surface 846. Accordingly, the disinfecting chamber 812 may be kept dry by means of the drip pan 806.

Figure 6:
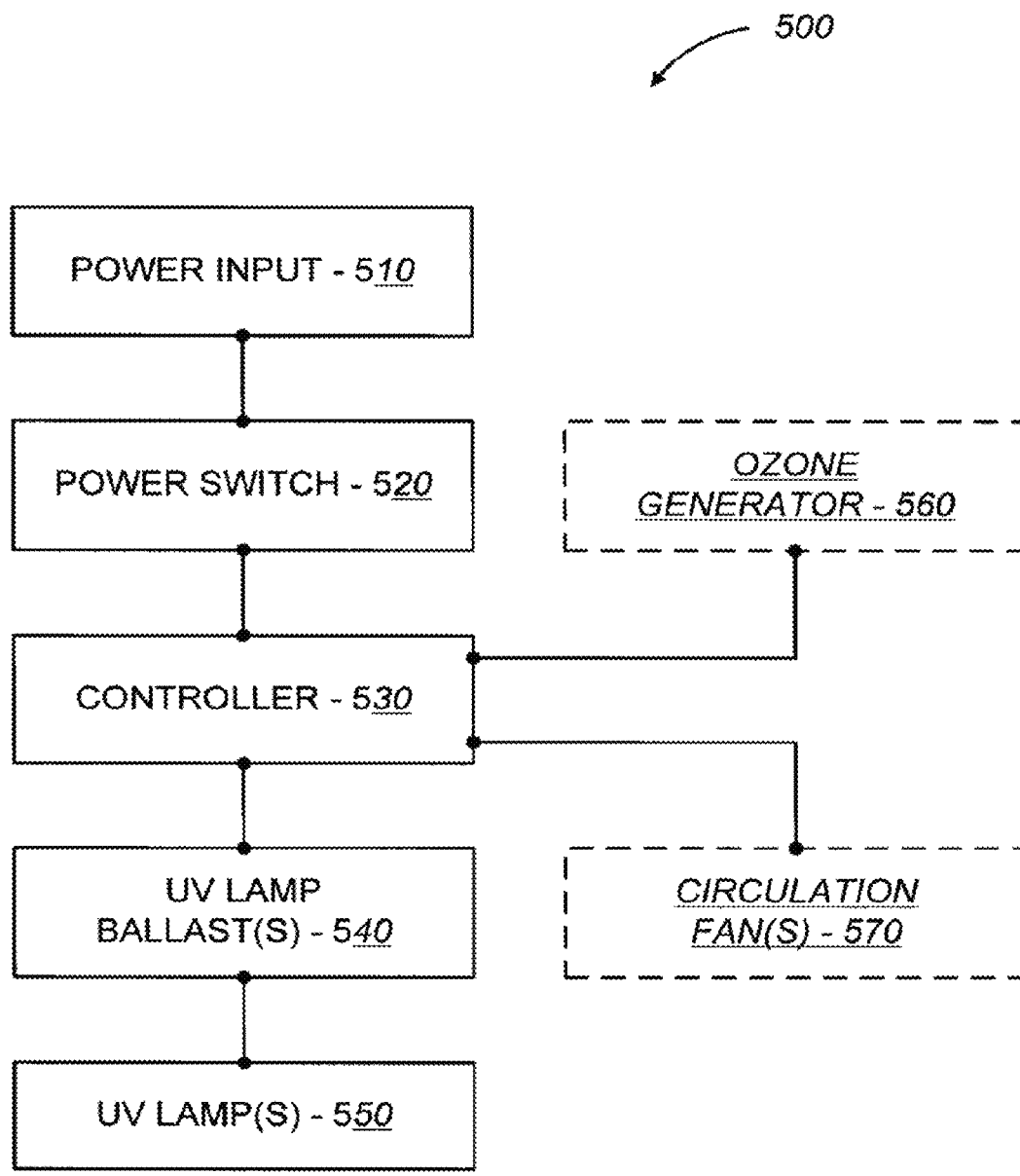
FIG. 6 is a simplified diagram illustrating an ultraviolet light disinfection system, in accordance with an embodiment of the present invention.

FIG. 6 is a simplified diagram illustrating an ultraviolet light disinfection system 500. The disinfection system 500 includes a power input 510, a power switch 520, a controller 530, an ultraviolet lamp ballast(s) 540, and an ultraviolet lamp(s) 550. The disinfection system 500 can also include optional additional components such as an ozone generator 560 and/or a circulation fan(s) 570.

The power input 510 receives electrical power (e.g., alternating current from an external source, direct current from an external source, direct current from a internal battery) used to operate the disinfection system 500. The power input 510 can transfer the received power directly. If required by the operational needs of the disinfection system, the power input can also convert the received power into one or more forms used by components of the disinfection system (e.g., into a DC voltage suitable to operate digital circuitry in the controller; into any form required to operate the lamp ballast(s) 540, the lamp(s) 550, the ozone generator 560, and/or the circulation fan(s) 570). In many embodiments, the power switch is an on/off switch used to activate and deactivate the disinfection system.

In many embodiments, the controller 530 is configured to periodically activate the UV lamp(s) 550 to maintain a food or beverage dispenser in a disinfected state. For example, the controller can include an interval timer that provides a periodic application of power to the lamp ballast(s) 540. The controller can be implemented in any suitable manner (e.g., using analogue components, using digital components, a mix of analogue and digital components). The controller can also be programmable through, for example, a suitable user interface and/or communication channel.

While the above-discussed embodiments involve certain types of beverage dispensers, the present invention is not limited to such beverage dispensers. For example, contained ultraviolet light can be applied to other types of beverage dispensers and/or food dispensers. Such food dispensers include, for example, a hot cheese dispenser (e.g., as described in U.S. Patent Publication No. 2009-023544 A1, the entire disclosure of which is incorporated herein by reference); a refrigerated milk dispenser (e.g., as described in U.S. Pat. No. 6,832,487, the entire disclosure of which in incorporated herein by reference); a pizza sauce dispenser (e.g., as described in U.S. Pat. No. 7,074,277, the entire disclosure of which is incorporated herein by reference); and a liquid egg dispenser (e.g., as described in U.S. patent application Ser. No. 11/763,992, the entire disclosure of which is incorporated herein by reference).

Figure 7:
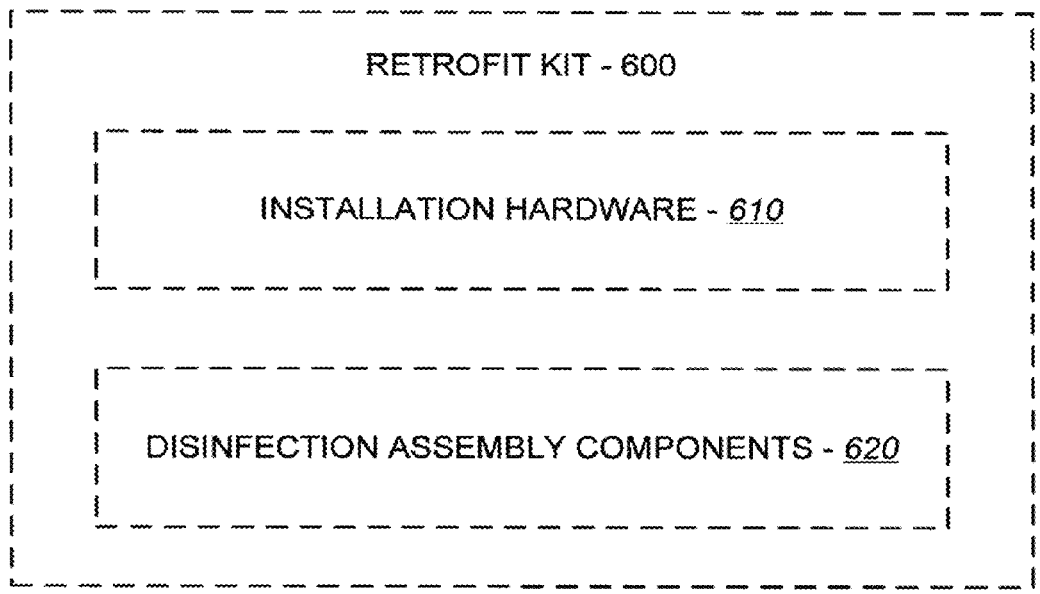
FIG. 7 is a simplified diagram illustrating a retrofit kit for retrofitting an ultraviolet light disinfection system to a pre-existing food or beverage dispenser, in accordance with an embodiment of the present invention.
Figure 8A:
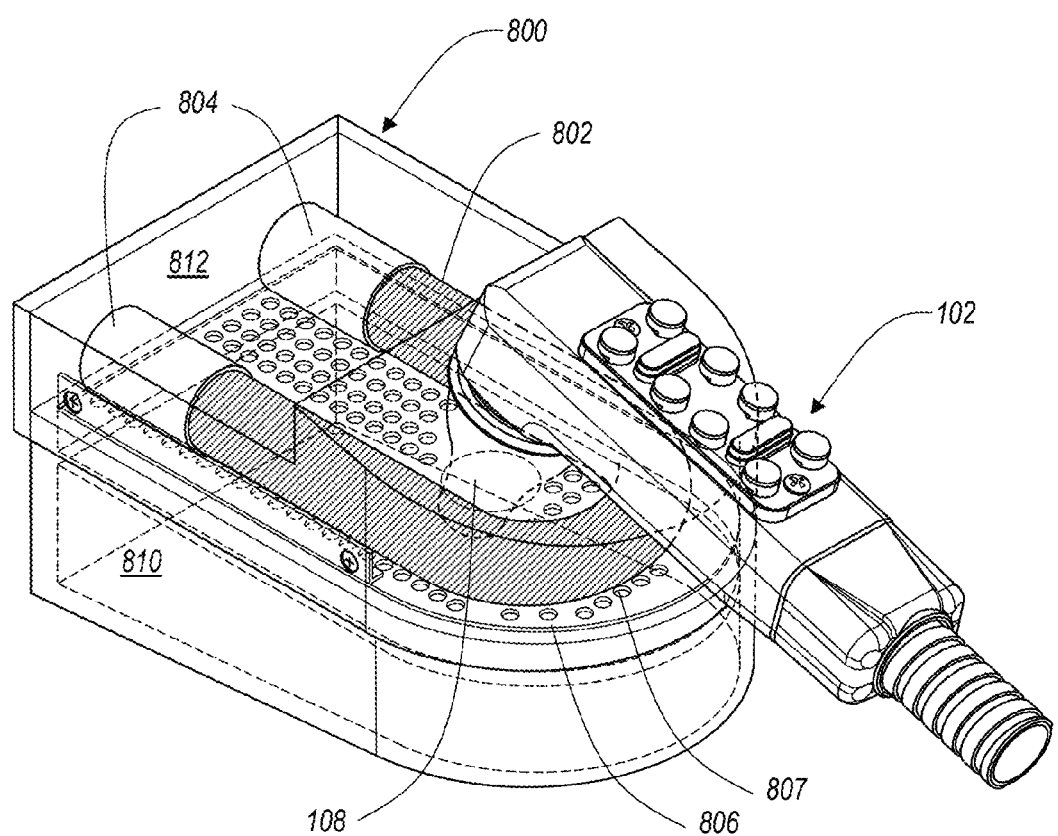
FIG. 8a through 8e illustrate various views of a bar gun holster configured to apply contained ultraviolet light to disinfect dispensing components of the bar gun, in accordance with an embodiment of the present invention.
Figure 8B:
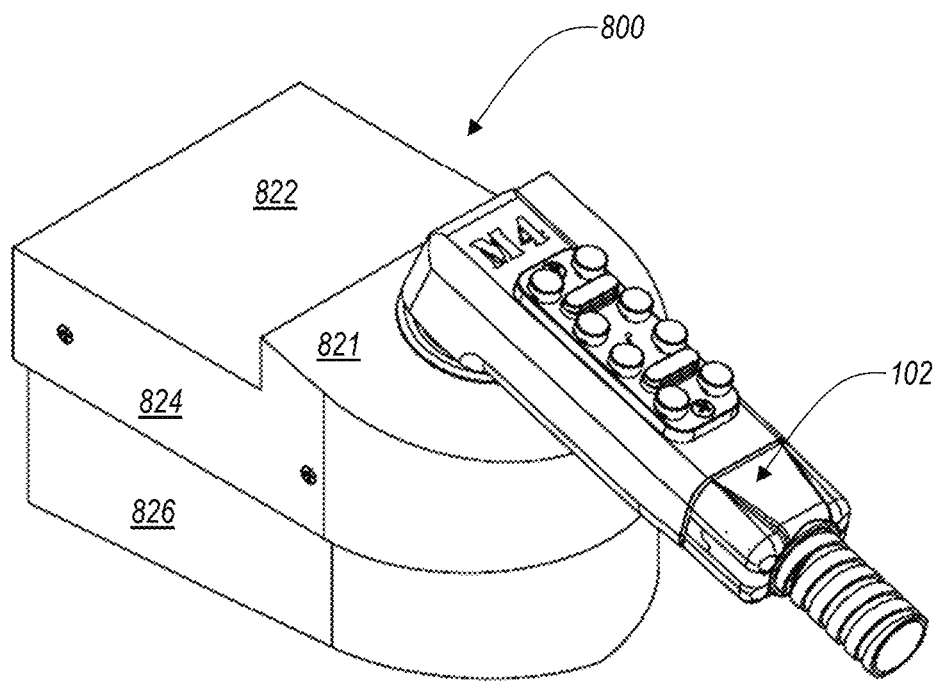
Figure 8C:
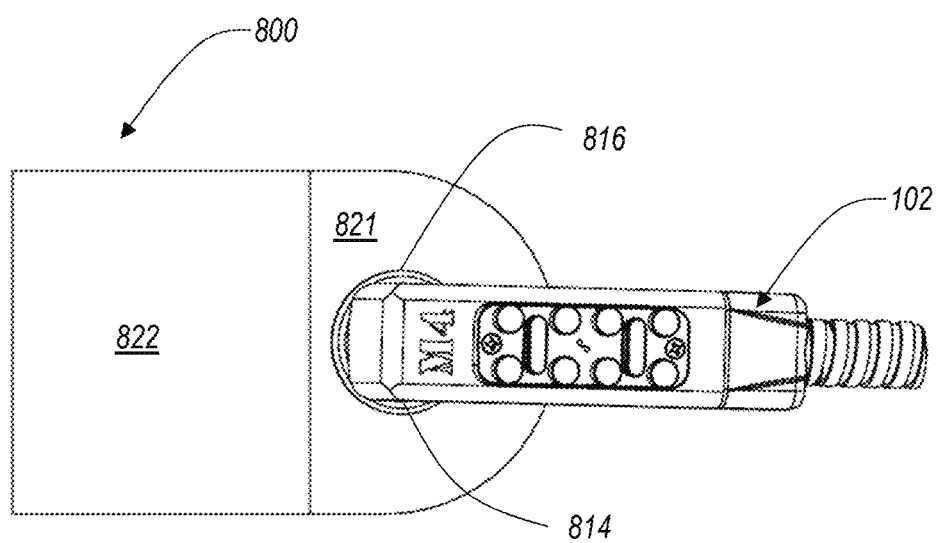
Figure 8D:
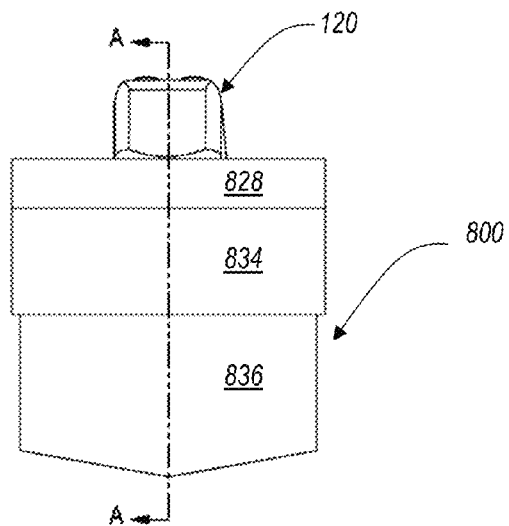
Figure 8E:
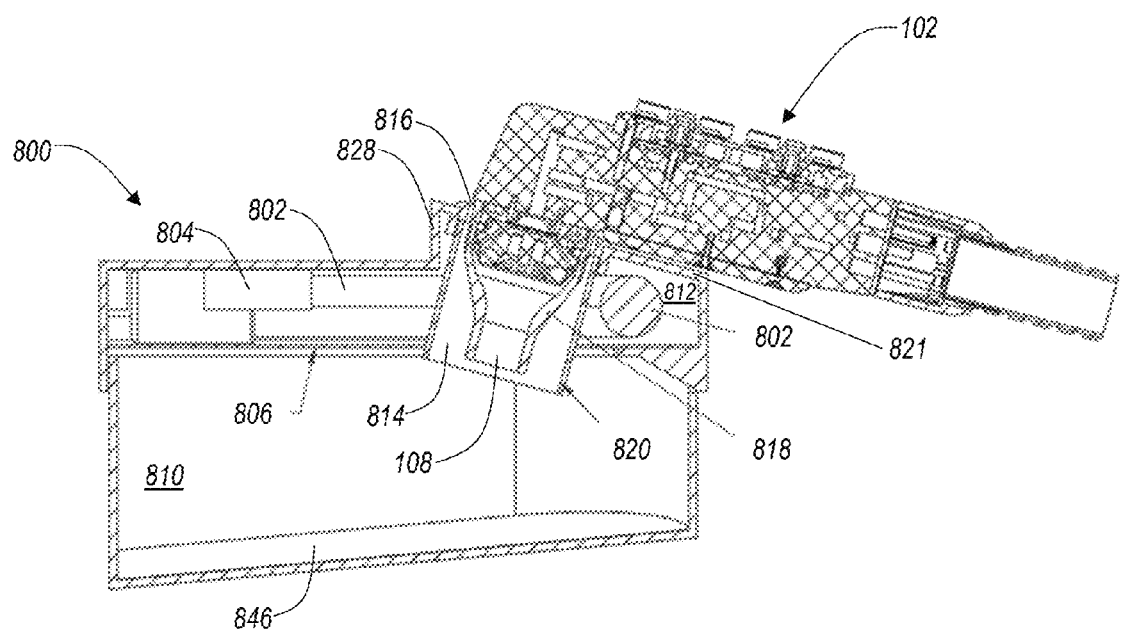

The disclosed disinfection devices and system can also be retrofitted to existing food or beverage dispensers. FIG. 7 is a simplified top-level diagram illustrating a retrofit kit 600 for retrofitting an ultraviolet light disinfection system to a pre-existing food or beverage dispenser. The retrofit kit 600 includes installation hardware 610 and disinfection assembly components 620. In many embodiments, the disinfection assembly components 620 include, for example, one or more ultraviolet light sources such as the UV lamp(s) 550, a housing/shield component(s) used to contain the ultraviolet light, and related electrical components such as the power input 510, the power switch 520, the controller 530, the UV lamp ballast(s) 540, and any related electrical connectors/ wires. A variety of retrofit kits can be configured for use on a wide variety of existing food and beverage dispensers. Each retrofit kit can be configured for use on one or more existing food and/or beverage dispenser types/models.

As will be understood by those skilled in the art, the present invention may be embodied in other specific forms without departing from the essential characteristics thereof. These other embodiments are intended to be included within the scope of the present invention, which is set forth in the following claims.

What is claimed is:

1. A disinfecting holster for a nozzle of a beverage dispensing handle, the disinfecting holster comprising:
   a housing adapted to receive a nozzle of a beverage dispensing handle;
   an ultraviolet light source arranged around an exterior wall of the housing to surround at least a portion of the exterior wall of the housing, the ultraviolet light source configured to generate and emit germicidal ultraviolet light onto the nozzle; and
   a first enclosure defining a first chamber, wherein the housing extends through the first chamber, wherein the first chamber contains the ultraviolet light source, the first enclosure having a top surface including a nozzle opening aligned with the housing and configured to hold the nozzle of the beverage dispensing handle such that only the nozzle extends into the housing.

2. The disinfecting holster of claim 1, wherein the ultraviolet light source is a U-bend ultraviolet light source.

3. The disinfecting holster of claim 1, wherein the ultraviolet light source is an O-ring ultraviolet light source.

4. The disinfecting holster of claim 1, wherein the ultraviolet light source is formed of a plurality of ultraviolet light source modules that surround at least the portion of the housing.

5. The disinfecting holster of claim 1, wherein an interior of the housing is formed of or lined with food-grade ultraviolet-transmissive plastic.

6. The disinfecting holster of claim 1, wherein an exterior of the housing is formed of or lined with transmissive quartz sleeve to protect the ultraviolet light source from spatters coming out of the nozzle.

7. The disinfecting holster of claim 1, wherein the first enclosure is formed on top of a second enclosure defining a second chamber, wherein the first enclosure and the second enclosure are separated by a perforated surface provided at a bottom of the first enclosure.

8. The disinfecting holster of claim 7, wherein the perforated surface is formed of or lined with reflective material to reflect the germicidal ultraviolet light into an orifice of the nozzle.

9. The disinfecting holster of claim 7, wherein the first enclosure further includes a fan to distribute ozone generated by the germicidal ultraviolet light within the first enclosure and the housing.

10. The disinfecting holster of claim 1, further comprising a controller configured to periodically activate the ultraviolet light source to maintain the nozzle in a disinfected state.

11. The disinfecting holster of claim 1, wherein the ultraviolet light source is manually activated to maintain the nozzle of the beverage dispensing handle in a disinfected state.

12. The disinfecting holster of claim 1, wherein the top surface extends over the ultraviolet light source.

13. An apparatus for disinfecting a nozzle of a beverage dispensing handle, the apparatus comprising:
   a housing adapted to receive a nozzle of a beverage dispensing handle;
   an ultraviolet light source arranged around at least a portion of the housing, the ultraviolet light source configured to generate and emit germicidal ultraviolet light onto the nozzle;
   a first enclosure defining a first chamber, wherein the housing extends through the first chamber, wherein the first chamber contains the ultraviolet light source, the first enclosure having a top surface including a nozzle opening aligned with the housing and configured to hold the nozzle of the beverage dispensing handle such that only the nozzle extends into the housing; and
   a second enclosure defining a second chamber provided below the first enclosure, the second enclosure being separated from the first enclosure by a perforated surface,
   wherein an interior of the housing is formed of or lined with food-grade ultraviolet-transmissive plastic, and an exterior of the housing is formed of or lined with transmissive quartz sleeve to protect the ultraviolet light source from spatters coming out of the nozzle.

14. A method for disinfecting a nozzle of a beverage dispensing handle, the method comprising:
   receiving a nozzle of a beverage dispensing handle in a housing, wherein an ultraviolet light source is arranged around an exterior wall of the housing to surround at least a portion of the exterior wall of the housing; and
   emitting germicidal ultraviolet light generated by the ultraviolet light source onto the nozzle,
   wherein the ultraviolet light source in provided within a chamber that substantially contains the germicidal ultraviolet light and the germicidal ultraviolet light is generated and emitted by the ultraviolet light source with a duration and an intensity selected to disinfect the nozzle,
   wherein the housing extends through the chamber that contains the ultraviolet light source, the chamber having a top surface including a nozzle opening aligned with the housing and configured to hold the nozzle of the beverage dispensing handle such that only the nozzle extends into the housing.

15. The method of claim 14, wherein the ultraviolet light source is a U-bend ultraviolet light source.

16. The method of claim 14, wherein the ultraviolet light source is an O-ring ultraviolet light source.

17. The method of claim 14, wherein the step of emitting germicidal ultraviolet light generated by the ultraviolet light source onto the nozzle comprises controlling an activation of the ultraviolet light source via a controller configured to periodically activate the ultraviolet light source to maintain the nozzle in a disinfected state.

18. The method of claim 14, wherein the step of emitting germicidal ultraviolet light generated by the ultraviolet light source onto the nozzle comprises manually initiating emission of the germicidal ultraviolet light.

19. The method of claim 14, wherein the step of emitting germicidal ultraviolet light generated by the ultraviolet light source onto the nozzle comprises emitting the germicidal ultraviolet light from a plurality of ultraviolet light source modules distributed around the housing.

20. The method of claim 14, wherein an interior of the housing is formed of or lined with food-grade ultraviolet-transmissive plastic.

21. The method of claim 14, wherein an exterior of the housing is formed of or lined with transmissive quartz sleeve to protect the ultraviolet light source from spatters coming out of the nozzle.

\* \* \* \* \*